(12) United States Patent
Corson et al.

(10) Patent No.: US 7,331,511 B2
(45) Date of Patent: Feb. 19, 2008

(54) BIOPOLYMERIC ARRAY SCANNERS CAPABLE OF AUTOMATIC SCALE FACTOR SELECTION FOR A PLURALITY OF DIFFERENT DYES, AND METHODS FOR MAKING AND USING THE SAME

(75) Inventors: John F. Corson, Mountain View, CA (US); Scott D. Connell, Pinckney, MI (US); Srinka Ghosh, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 549 days.

(21) Appl. No.: 10/328,109

(22) Filed: Dec. 23, 2002

(65) Prior Publication Data

US 2004/0121483 A1 Jun. 24, 2004

(51) Int. Cl.
*G06F 17/00* (2006.01)
(52) U.S. Cl. ..................................... 235/375
(58) Field of Classification Search ................ 235/454, 235/375; 250/394
See application file for complete search history.

(56) References Cited

U.S. PATENT DOCUMENTS

| | | | |
|---|---|---|---|
| 5,091,652 A | 2/1992 | Mathies et al. | |
| 5,260,578 A | 11/1993 | Bliton et al. | |
| 5,296,700 A | 3/1994 | Kumagai | |
| 5,324,633 A | 6/1994 | Fodor et al. | |
| 5,509,086 A * | 4/1996 | Edgar et al. | 382/167 |
| 5,585,639 A | 12/1996 | Dorsel et al. | |
| 5,760,951 A | 6/1998 | Dixon et al. | |
| 5,763,870 A | 6/1998 | Sadler et al. | |
| 6,084,991 A | 7/2000 | Sampas | |
| 6,222,664 B1 | 4/2001 | Dorsel | |
| 6,284,465 B1 | 9/2001 | Wolber | |

(Continued)

FOREIGN PATENT DOCUMENTS

WO   WO 00/16087   3/2000

(Continued)

OTHER PUBLICATIONS

Li et al. Abstract 27 Fully Automated Multiplexed Capillary Systems for DNA Sample Analysis., DOE Human Genome Program, Contractor-Grantee Workshop VIII ( Feb. 27 to Mar. 2, 2000) Santa Fe, NM.

(Continued)

*Primary Examiner*—Jamara A. Franklin

(57) ABSTRACT

Biopolymeric array scanners that are capable of automatically selecting a dye specific scale factor to employ for a plurality of different dyes, as wells as methods for making and using the same, are provided. In many embodiments, the actual dye specific scale factor automatically selected by the scanner is one that is equal to a preset "master" scale factor, so that the scanner reads any supported dye using the same constant scale factor. The dye specific scale factor selection is typically made by reference to a collection of nominal scale factors for each member of the plurality of dyes. In using the subject scanners, a user simply inputs the one or more dyes being used in a given array assay, and the scanner automatically reads the array using an automatically chosen dye specific scale factor for the selected dyes. Also provided are methods of obtaining collections of nominal scale factors and computer readable mediums comprising the same. The subject invention finds use in a variety of different applications, including both genomics and proteomics applications.

12 Claims, 1 Drawing Sheet

U.S. PATENT DOCUMENTS

| | | |
|---|---|---|
| 6,320,196 B1 | 11/2001 | Dorsel et al. |
| 6,335,934 B1 | 1/2002 | Sakurai et al. |
| 6,371,370 B2 | 4/2002 | Sadler et al. |
| 6,448,564 B1 * | 9/2002 | Johnson et al. ............. 250/394 |
| 6,558,945 B1 * | 5/2003 | Kao ........................ 435/287.2 |
| 6,897,954 B2 * | 5/2005 | Bishop et al. .............. 356/317 |
| 6,958,811 B2 * | 10/2005 | Wolleschensky et al. ... 356/326 |
| 2002/0164817 A1 * | 11/2002 | Neriishi ...................... 436/172 |
| 2004/0005243 A1 * | 1/2004 | Mulhern et al. .............. 422/58 |

OTHER PUBLICATIONS

C. Domnisoru et al. "Filtering Technique for Fluorescence-Based DNA Sequencing Data," 2000 Canadian Conference on Electrical and Computer Engineering (2000) 1:489-493.

Li et al. "An Estimate of the Crosstalk Matrix in Four-Dye Fluorescence-Based DNA Sequencing," Electrophoresis (1999) 20:1433-1442.

Kheterpal et al. "DNA Sequencing Using a Four-Color Confocal Fluorescence Capillary Array Scanner," Electrophoresis (1996) 17:1852-1859.

Yin et al. "Automatic Matrix-Determination in Four Dye Fluorescence-Based DNA Sequencing," Electrophoresis (1996) 17:1143-1150.

Domnisoru et al. "Cross-Talk Filtering in Four Dye Fluorescence-Based DNA Sequencing," Electrophoresis (2000) 21:2983-2989.

* cited by examiner

BIOPOLYMERIC ARRAY SCANNERS CAPABLE OF AUTOMATIC SCALE FACTOR SELECTION FOR A PLURALITY OF DIFFERENT DYES, AND METHODS FOR MAKING AND USING THE SAME

FIELD OF THE INVENTION

This invention relates generally to optical scanners and, more particularly, to optical array scanners.

BACKGROUND OF THE INVENTION

Array assays between surface bound binding agents or probes and target molecules in solution are used to detect the presence of particular biopolymers in a sample. The surface-bound probes may be oligonucleotides, peptides, polypeptides, proteins, antibodies or other molecules capable of binding with target molecules of interest in solution. Such binding interactions are the basis for many of the methods and devices used in a variety of different fields, e.g., genomics (in sequencing by hybridization, single nucleotide polymerase (SNP) detection, differential gene expression analysis, identification of novel genes, gene mapping, finger printing, etc.) and proteomics.

One typical array assay method involves biopolymeric probes immobilized in an array on a substrate. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The binding by target molecules to biopolymer probe features or spots on the substrate produces a pattern on the surface of the substrate and provides desired information about the sample. In most instances, the target molecules are labeled with a detectable tag such as a fluorescent tag or chemiluminescent tag.

The resultant binding interaction or complexes of binding pairs are then detected and read or interrogated, for example by optical means, although other methods may also be used. Typically, imaging devices or analogous instruments designed to map the density of sample adhered to a biopolymer array are employed to read an array. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many array-based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

The scanning equipment typically used for the evaluation of arrays includes a scanning fluorometer. A number of different types of such devices are commercially available from different sources, such as Perkin-Elmer, Agilent, or Axon Instruments., etc. Analysis of the data, (i.e., collection, reconstruction of image, comparison and interpretation of data) is performed with associated computer systems and commercially available software, such as Quantarray™ by Perkin-Elmer, Genepix Pro™ by Axon Instructions, Microarray Suite™ by Affymetrix, as well as Feature Extraction Software and Rosetta Resolver Gene Expression Data Analysis System, both available from Agilent.

In such devices, a light source (e.g., a laser light source) generates an excitation light, e.g., a collimated beam. The excitation light is focused on the array and sequentially illuminates small surface regions of known location on an array substrate. The resulting fluorescence signals from the surface regions are collected employing the same lens used to focus the laser light onto the array, or off-axis (using a separate lens positioned to one side of the lens used to focus the laser onto the array). The collected signals are then typically transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". In obtaining array data, an important parameter is the scale factor of the scanner. The scale factor is defined as the number of signal counts that are reported to the user per chromophore per area on the array, e.g., counts in a 10 micron pixel/chromophore per square micron. Different chromophores or dyes employed in array-based applications typically have different scale factors for a given detection system. For a scanner this would mean that different dyes would have a different scale factors even for equivalent detector gain and intensity of excitation light. This variation in the scale factor for different dyes depends a given dye's quantum efficiency, extinction coefficient, excitation and emission spectra.

Typically, the scale factor employed by a scanner during use is programmed or set for a specific dye or dyes during manufacturing of the scanner. This programming or setting is done by fixing the detector gain (i.e. voltage for a photo-multiplier tube (PMT) detector) or by varying the intensity of the excitation light incident on the array. For example, where a scanner is designed to read an array in two different channels, the scanner is typically programmed to employ a given gain setting to obtain a first scale factor in the first channel and another gain setting to obtain a second scale factor in the second channel, where the programmed scale factors are those that are appropriate for specific first and second dyes, e.g., Cy3 and Cy5. Such preprogramming usually ensures that the same scale factor is employed for each of the two supported dyes each time an array is scanned. Obtaining equal scale factors for different dyes generally requires different gain settings for each dye for the reasons described above. In some cases different scale factors can intentionally be set for different dyes. Problems with such preprogrammed scanners may arise where a user employs a scanner with dyes other than the dyes for which the scanner was initially programmed. For example, in scanners that are set or programmed for use with Cy3 and Cy5, other markers can be employed in such scanners, but the readings obtained therefrom will be readings that are taken with Cy3 and Cy5 scale factors. The scale factors for the specific dyes employed may be different and may not be appropriate. As such, errors in terms of actual intensity and its relation to the density of targets may be introduced, thereby skewing the obtained results. Further, if the scale factor for a specific dye is different enough it may lead to signals saturating the detector or falling below the detection limit of the scanner.

Currently, where users wish to employ a scanner with dyes other than those for which the scanner is designed, the user must make manual changes to the detector gain (i.e.

change PMT voltage) to maintain constant scale factor. Alternatively, users can normalize obtained data after scanning to remove errors introduced by the incorrect scale factor. This post-scan normalization step may not be possible if the scan is saturated or below the detection limit due to a substantially different scale factor While the above approaches may remove many of the errors introduced by incorrect scale factor usage, they require additional steps. As such, there is interest in the development of scanners that can be used with a plurality of different dyes, where the scanner is capable of automatically selecting a correct scale factor to use for a given dye during the scan. The present invention satisfies this, and other, needs.

Relevant Literature

United States Patents of interest include: U.S. Pat. No. 5,091,652; 5,260,578; 5,296,700; 5,324,633; 5,585,639; 5,760,951; 5,763,870; 6,084,991; 6,222,664; 6,284,465; 6,317,370 6,320,196 and 6,355,934. See also Li et al., Abstract 27. Fully Automated Multiplexed Capillary Systems for DNA Sample Analysis, DOE Human Genome Program, Contractor-Grantee Workshop VIII (Feb. 27 to Mar. 2, 2000) Santa Fe, N.M.

SUMMARY OF THE INVENTION

Biopolymeric array scanners that are capable of automatically selecting a dye specific scale factor to employ for a plurality of different dyes, as well as methods for making and using the same, are provided. In many embodiments, the actual dye specific scale factor automatically selected by the scanner is one that is equal to a preset "master" scale factor, so that the scanner reads any supported dye using the same constant scale factor. The dye specific scale factor selection is typically made by reference to a collection of nominal scale factors for each member of the plurality of dyes. In using the subject scanners, a user simply inputs the one or more dyes being used in a given array assay, and the scanner automatically reads the array using an automatically chosen dye specific scale factor for the selected dyes. Also provided are methods of obtaining collections of nominal scale factors and computer readable mediums comprising the same. The subject invention finds use in a variety of different applications, including both genomics and proteomics and other fluorescence based applications.

DEFINITIONS

Figure 1:
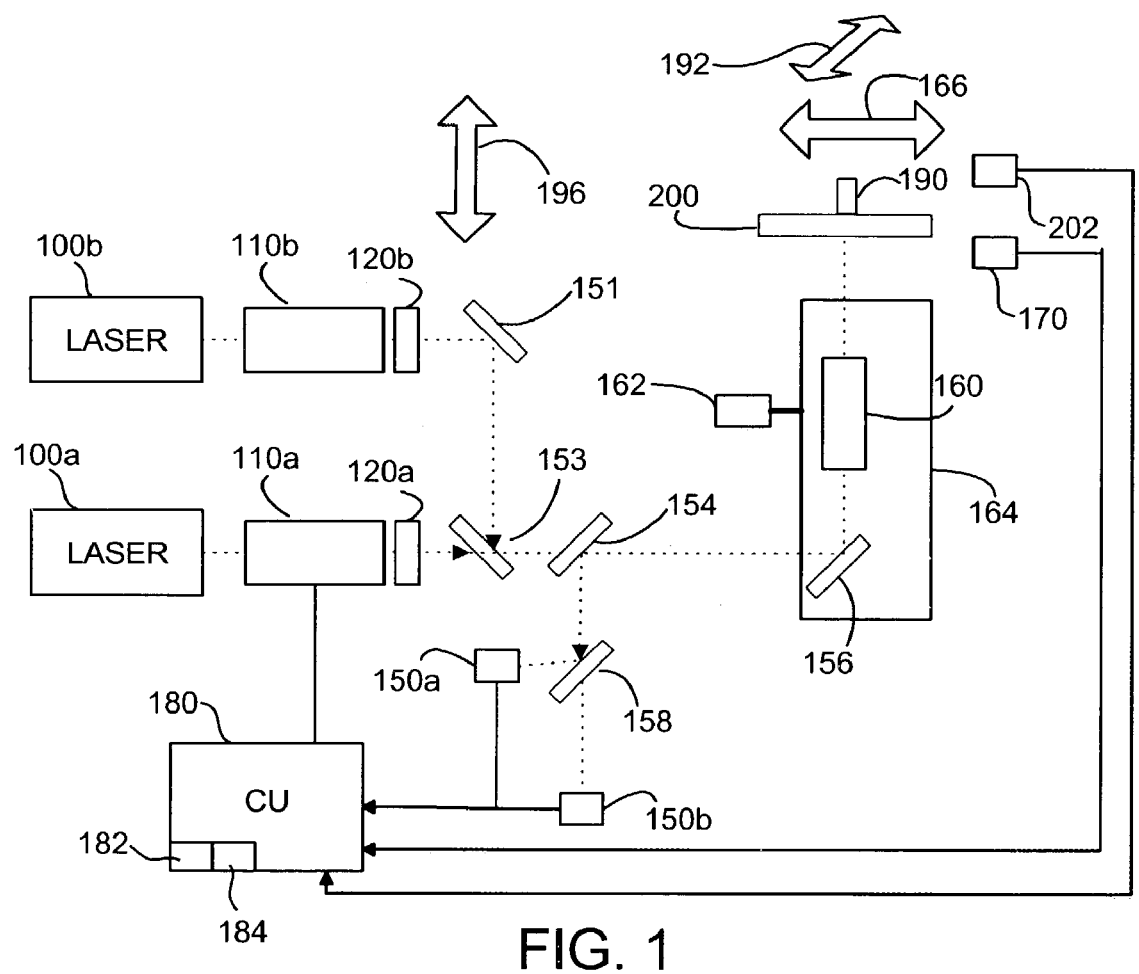
FIG. 1 provides a schematic view of a representative optical biopolymeric array scanning device according to the subject invention.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups.

Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions.

Polynucleotides include single or multiple stranded configurations, where one or more of the strands may or may not be completely aligned with another.

A "nucleotide" refers to a sub-unit of a nucleic acid and has a phosphate group, a 5' carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source.

An "oligonucleotide" generally refers to a nucleotide multimer of about 10 to 100 nucleotides in length, while a "polynucleotide" includes a nucleotide multimer having any number of nucleotides.

A "biomonomer" references a single unit, which can be linked with the same or other biomonomers to form a biopolymer (e.g., a single amino acid or nucleotide with two linking groups one or both of which may have removable protecting groups).

An "array," includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more arrays disposed on a front surface of the substrate. Depending upon the use, any or all of the arrays may be the same or different from one another or maybe a continuation of the other as in the case of a particular genome being extended across two or more arrays and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse-jets of either polynucleotide precursor units (such as monomers) in the case of in situ fabrication, or the previously obtained polynucleotide. Such methods are described in detail in, for example, the previously cited references including U.S. Pat. Nos. 6,242,266; 6,232,072; 6,180,351; 6,171,797; and 6,323,043; as well as in U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. Nos. 5,599,695; 5,753,788; and 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination, which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

A "scanner" is a device for evaluating arrays. In scanners, an optical light source, particularly a laser light source, generates a collimated beam. The collimated beam is focused on the array and sequentially illuminates small surface regions of known location (i.e. a position) on an array substrate. The resulting signals from the surface regions are collected either—by employing the same lens used to focus the light onto the array or off-axis (using a separate lens positioned to one side of the lens used to focus the onto the array) or a variation of these approaches. The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". Biopolymer arrays are often scanned and/or scan results are often represented at 5 or 10 micron pixel resolution. To achieve the precision required for such activity, components such as the lasers must be set and maintained with particular alignment. Scanners may be bi-directional, or unidirectional, as is known in the art.

The scanner typically used for the evaluation of arrays includes a scanning fluorometer. A number of different types of such devices are commercially available from different sources, such as such as Perkin-Elmer, Agilent, or Axon Instruments, etc., and examples of typical scanners are described in U.S. Pat. Nos. 5,091,652; 5,760,951, 6,320,196 and 6,355,934.

DETAILED DESCRIPTION OF THE INVENTION

Biopolymeric array scanners that are capable of automatically selecting a dye specific scale factor to employ for a plurality of different dyes, as wells as methods for making and using the same, are provided. In many embodiments, the actual dye specific scale factor automatically selected by the scanner is one that is equal to a preset "master" scale factor, so that the scanner reads any supported dye using the same constant scale factor. The dye specific scale factor selection is typically made by reference to a collection of nominal scale factors for each member of the plurality of dyes. In using the subject scanners, a user simply inputs the one or more dyes being used in a given array assay, and the scanner automatically reads the array using an automatically chosen dye specific scale factor for the selected dyes. Also provided are methods of obtaining collections of. nominal scale factors and computer readable mediums comprising the same. The subject invention finds use in a variety of different applications, including both genomics and proteomics applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events, which are logically possible, as well as the recited order of events.

Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, process or program aspects of the invention are first described. This discussion is followed by a description of suitable hardware for use in the invention as well as use of such hardware in array-based applications, e.g., genomics and proteomics applications.

Methodology/Programming

As summarized above, the subject invention provides scanners that automatically select a dye specific scale factor to employ for a given dye, as well as methods for making and using such scanners. While the invention is described in terms of scanners and fluorescent dyes as an illustrative embodiment, the subject methodologies and composition find use with any multi channel optical detector and any optically detectable collection of labels. For example, in addition to multichannel optical scanner devices, as described in detail below, the subject methods are equally applicable to use with other types of multichannel optical detectors, e.g., a 2-dimensional CCD array device. Likewise, the subject methodology may also be employed with other optically detectable labels, such as chemilluminescent labels. A feature of the subject scanners is that during use, as described below in greater detail—, a user inputs into the scanner the one or more dyes that are to be used in a given assay, and the scanner then automatically selects the appropriate dye specific scale factor(s) to use in the assay based on the user input dye selection. In many embodiments, the selected dye specific scale factors are ones that equal a preset "master" scale factor, so that each of the input dyes is read at the same constant scale factor. Typically, a scanner selects the dye specific scale factor(s) to use in a given assay by referencing a collection of pre-obtained nominal scale factors for a plurality of different dyes, as further described below. Since a collection of nominal scale factors is employed in many embodiments of the subject invention, this aspect of the invention is now described in greater detail first, followed by a further review of how this collection is employed to automatically select a dye specific scale factor.

Obtaining a Collection of Nominal Scale Factors

Many embodiments of the subject invention employ a collection of nominal scale factors for a plurality of different dyes or labels. The term "nominal scale factor" refers to the measured counts per dye density for a given dye using a scanner whose gain is set at a nominal value. In a given collection of nominal scale factors according to the subject invention, each member nominal scale factor of the collection is one that is obtained by measuring the counts observed for a given number of chromophores in a given area in the same scanner, where the gain of the scanner is set at the nominal value. The nominal gain value employed in determination of the nominal scale factor of a given dye may vary, but typically ranges from that gain which yields for a standard dye (e.g. Cy3) a scale factor of about 0.1 to about 1000 counts per chromophore per square micron, usually from about 1 to about 100 counts per chromophore per square micron.

As indicated above, a plurality of different dyes are represented in a given collection of nominal scale factors, where the term "plurality" means at least 2 but typically means at least 3, usually at least about 5, at least about 10, at least about 15 or more, where the number of different dyes represented in a given collection may be at least about 25, at least about 50, or more. As such, by plurality is meant 2 or more, usually three or more, where in many embodiments, the number of different dyes having a nominal scale factor present in the collection, i.e., the number of different dyes represented in the collection of scale factors, ranges from about 5 to about 100, usually from about 10 to about 75 and more usually from about 10 to about 50.

Specific dyes or labels of interest include fluorescent dyes or labels. Representative fluorescent dyes or labels that find use in array based applications and therefore that may be represented in the subject collections of nominal scale factors include, but are not limited to: fluorescein, rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), the cyanine dyes, such as Cy3, Cy5, Alexa dyes covering a variety of wavelengths, Bodipy 630/650, fluorescent particles, fluorescent semiconductor nanocrystals, and the like.

In certain embodiments, the collection of nominal scale factors further includes, in addition to the collection of nominal scale factors, first order crosstalk data or information, i.e., characteristics, for each dye represented in the collection. By first order crosstalk is meant the off-diagonal terms linking a dye in a first measurement channel of a scanner device into the observed signal in a second measurement channel of a scanner device, and vice versa. In other words, first order crosstalk is a measure or quantification of the amount of signal generated by a given dye in a measurement channel of the device that is not intended to measure the dye, but is intended to measure the signal of a different dye. For example, in a device where the first measurement channel is set up to measure red signal and the second measurement channel is set up to measure green signal, the first order crosstalk of a given dye that emits a red signal is the amount of signal observed from the given red emitting dye in the green channel. First order crosstalk can also be measured and included for more than 2 detectors. For instance, for a four detector system, the first order crosstalk for each dye can be measured between the dye and the three other detectors not intended for measuring that dye.

In these collections of data or information that include both nominal scale factors and first order crosstalk chracteristics for each dye member represented in the collection, the information may be represented by a matrix of the following type:

|Signal Channel 1|=|Scale Factor 1 CrossTalk
  1-2|*|Dye 1 Density|

|Signal Channel 2|=|CrossTalk 2-1 Scale Factor 2|
  |Dye 2 Density|

For example, for Cy3 (Dye 1) and Cy5 (Dye 2), a representative matrix might be: top column (60 0.01) bottom column (0.05 40).

To determine the off-axis elements, representing first order crosstalk, many methods obvious to one skilled in the art exist. One example would be to scan reference slides with purely one dye in the scanner. Then one would scan a bare substrate with no dye. The first order crosstalk associated with this dye going into the other dye's channel would then be the difference in signal in the non-intended channel between the bare substrate and the slide coated in the dye.

To produce a given collection of nominal scale factors, a nominal scale factor for each dye or label that is to be represented in the collection, i.e., that is to have a nominal scale factor in the collection, is obtained. As such, for each dye to be represented in the collection, the number of counts observed per dye density in a scanner is measured to obtain a nominal scale factor for the given dye. In such a process, the same scanner set at the same nominal gain is employed to determine the nominal scale factor for each dye to be represented in the collection. In other words, the scale factor for each dye to be represented in the collection is obtained using the same scanner having a gain set at the same nominal value.

To measure the nominal scale factor of a dye, a substrate having a known amount of the dye present on a surface thereof is provided and then scanned in an array scanning instrument, where the scanning instrument has its gain set to the nominal value. Any convenient scanner may be employed to produce a given collection, including the scanner devices described in the specific scanner patents referenced below. The nominal scale factor for the dye is then determined by measuring the counts/dye density, e.g., by measuring the number of counts in a 10 µm pixel/dye (chromophore) per µm$^2$. More generally, the amount of counts per density of dye can be averaged over a larger area and then normalized by the number of pixels included. This larger area could be 10 or 100 or 1000 or 10000 or more pixels. This approach will provide a better measurement of the nominal scale factor by averaging over many pixels. This approach will help to minimize noise in the measurement generated by local non-uniformities in the dye density.

In those embodiments where the collection further includes first order crosstalk data or information for each dye represented in the collection, the above protocol for producing the subject collections further includes determining the first order crosstalk observed for each dye member along with the nominal scale factor.

Scanner Selection of Dye Specific Scale Factor

As summarized above, a feature of array scanners of the subject invention is that the array scanners can automatically select or determine a dye specific scale factor to use in a given assay, where the dye specific scale factor is selected or chosen by the scanner based on the actual dyes employed in a given assay. In other words, knowledge of the actual dyes to be used in a given assay is employed by the scanner device to automatically select a dye specific scale factor to employ in the assay. As such, the subject invention is contrasted from other scanner devices in which the scale factor employed in a given assay is one that is pre-selected during manufacture of the scanner and is not influenced, i.e., selected, based on the actual dyes to be employed in a given assay.

To provide for the above feature, the subject invention provides methodology/programming that directs a scanner to select a dye specific scale factor(s) based on input dye(s) choices. The subject programming/methodology (e.g., in the form of an algorithm) directs a scanner to select a dye specific scale factor to use in a given assay based on, i.e., in view of, the actual dye or dyes being employed in a given assay. As such, in response to input of the one or more actual dyes that are employed in a given assay, the subject methodology/programming selects an appropriate dyes specific scale factor to employ in an assay in which the input dye(s) is employed.

In many embodiments, the dye specific scale factor chosen by the scanner for a given dye is a scale factor that is equal to a preset or predetermined "master" scale factor. In other words, the scanner automatically chooses an actual scale factor based on a particular dye selection (a dye specific actual scale factor), where the actual scale factor is the same as a predetermined master scale factor. For example, where dye 1 and dye 2 are to be employed in a given assay, the user will input this selection of dye 1 and dye 2 into the scan. The scanner will then automatically employ an actual scale factor for dye 1 in the first measurement channel that is the same as a predetermined master scale factor and will also automatically select and employ an actual scale factor for dye 2 that is the same as the predetermined scale factor, so that the actual scale factor for dye 1 and dye 2 are the same as the master scale factor.

In certain embodiments, e.g., where dyes have significantly different nominal scale factors, different "master" scale factors may be employed for different groups of dyes. For example, where a scanner is to be programmed for use with 10 different dyes, and dyes 1 to 5 have a nominal scale factor that is similar to each other but significantly different from the nominal scale factors of dyes 6 to 10, a first master scale factor can be employed for dyes 1 to 5 and a second master scale factor can be employed for dyes 5 to 10.

While the preset or predetermined master scale factor(s) employed by a given scanner may vary, the master scale factor typically ranges from about 0.1 to about 1000 counts per chromophore per square micron, usually from about 1 to about 100 counts per chromophore per square micron. In many embodiments, the subject programming selects the dye specific or actual scale factor to employ in a given assay by referencing a collection of nominal scale factors, as described above. More specifically, following input of the one or more dye choices to be used in a given assay, the subject programming then takes the input dye choices and identifies a nominal scale factor in a collection of scale factors for each dye choice. For example, where dye A and dye C are input, the programming then identifies the nominal scale factor for dye A and dye C in the collection of nominal scale factors for dyes A to Z. Following identification of the relevant nominal scale factor for each input dye, the programming then uses the identified nominal scale factors and the scanner instrument's known or internally calibrated correspondence between PMT voltage and instrument gain, to automatically adjust the scanner gain, e.g., via PMT voltage modulation or change) in each channel so that the actual scale factor for the input dyes is the same as the predetermined master scale factor, i.e., the device measures the same number of counts/dye density for each of the input dyes in each channel, which measurement is the same as the predetermined master scale factor.

In this manner, the programming selects a dye specific scale factor to employ in-a given assay for each dye employed in the assay based on the input dye selections for the given assay.

In those embodiments where a scanner with more than one measurement channel is employed and the collection further includes first order crosstalk characteristics for at least some of, if not all of, the dye members represented in the collection, as described above, the subject programming may also provide for adjusting the observed data in an assay to correct for first order crosstalk. In other words, the programming in these embodiments can further provide for first order crosstalk correction. following initial data acquisition in a given array assay. In certain embodiments, the programming corrects initially observed data for first order crosstalk by deconvolution of the following matrix:

|Signal Channel 1|=|Scale Factor 1 CrossTalk
   1-2|*|Dye 1 Density|

|Signal Channel 2|=|CrossTalk 2-1 Scale Factor 2|
   |Dye 2 Density|

While the above matrix may be deconvoluted for every feature or pixel observed in a given assay, in certain embodiments the above matrix is deconvoluted for only those features or pixels which have substantially the same signal levels, where substantially the same means that the signal levels do not vary from each other by more than about 1000 fold, usually by no more than about 100 fold and more usually by no more than about 10 fold and even more usually by no more than 5 fold. A feature of these particular embodiments in which deconvolution is only practiced for those features having substantially the same signal level is that the possibility of corrupting data in a channel with a low number of counts resulting from noise from a second channel with a high number of counts is minimized.

With respect to crosstalk, in certain situations the crosstalk of a dye into a signal measurement channel that is not its intended measurement channel may be so great as to saturate the signal in the unintended measurement channel. "Saturation" in this context means the signal level reaches and exceeds a preset maximum allowable level and is therefore capped at the maximum level. In these instances, the programming/methodology may automatically adjust the gain of the of the scanner instrument, upon detection of saturation in a given feature, to reduce the measured scale factor, e.g., by reducing the PMT voltage. Following removal of crosstalk contribution to the signal, e.g., by deconvulation and subtraction of the crosstalk contribution to the signal, as described above, the programming can then multiply the remaining signal by a constant equal to the inverse of the amount by which the gain was turned down to return the actual scale factor to the master scale factor.

Another correction can be made given knowledge of the crosstalk between the dyes being used. Imagine that the dye from channel 1 is considerably more dense than dye from channel 2 (10 or 100 or 1000) in a given feature. In the case, as is normal, that there is a component of noise which is proportional to signal, then the noise in channel 1 will greatly exceed the noise in channel 2. In the case where channel 1 noise is larger than channel 2 noise by a sufficient amount, the noise in the crosstalk from dye 1 into channel 2 may become equal to or even larger than the intrinsic noise in channel 2 from the signal from dye 2. This may mean that the noise from the crosstalk from dye 1 into channel 2 is more than 0.1 or 1.0 or 10.0 times the intrinsic noise in channel 2 in the absence of crosstalk.

Knowing the amount of crosstalk between many dyes with each channel present allows the system to determine when this situation is present. When it occurs, the scanner can lower the excitation level (e.g., by reducing exciting laser power) on the channel contributing the crosstalk and crosstalk noise which is interfering in the other channel. It can then re-scan the array with lower crosstalk noise from that dye into other channels. It could repeat this procedure for all channels in the system which are contributing crosstalk noise above a certain threshold (e.g., 0.01, 0.1, 1.0, 10.0 times the intrinsic noise in that channel) into another channel.

This adjustment required to eliminate this crosstalk noise prior to re-scanning could also be accomplished with attenuators or even movable or adjustable filters. For example, if dye 1 is adding too much crosstalk and crosstalk noise into channel 2 a filter could be placed in the channel 2 signal path which further blocks the crosstalk signal and noise from channel 1. This filter can exploit spectral differences between the emmision of the two dyes or spatial differences between their detection paths to preferentially block light from dye 1. Generally it is inadvisable to completely filter light from dye 1 out of channel 2, and vice versa, because doing so also entails blocking some signal from dye 2 from reaching channel 2. However, in cases where the crosstalk noise from channel 1 is greater than a certain threshold (as a ratio to the intrinsic noise in channel 2) then it may increase overall signal to noise to preferentially block light from dye 1 from reaching channel 2, even though it reduces the amount of light from dye 2 reaching channel 2. If the system is programmed with the crosstalk information described above, it can be programmed to rationally determine when this situation arises and introduce the needed filters appropriately. The exact ratio of noise from dye 1 crosstalk and dye 2 in channel 2 for which it becomes beneficial to introduce the filter depends on the details of the detection system, the spectra of the dye emissions, the magnitude of crosstalk and the level of the signals. Everything described above with reference to dye 1 and dye 2 and channel 1 and channel 2 can be generalized to switching this channels and dyes or considering additional numbers of dyes and channels.

The above crosstalk correction steps performed by certain embodiments of the subject programming provide for a number of benefits, including the ability to keep the actual scale factor equal to the master scale factor for every supported dye in the scanner, even after deconvolution and subtraction of crosstalk. In addition, the above protocols can reduce the chance of feature saturation due to crosstalk.

Additional General Considerations

The above programming regarding collections of nominal scale factors and/or routines to employ the same to automatically select a dye specific scale factor and/or remove crosstalk contribution to measured signal can be implemented in many different languages, or hardware circuits, in an almost limitless number of ways, using different modular organizations and control logic.

Computer Readable Mediums

Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above described methodology.

Optical Scanners

Also provided by the subject invention are biopolymer array optical scanners that are programmed as described above, i.e., to automatically select a dye specific scale factor for use in a given array assay based on input of one or more dye selections.

Any biopolymer optical scanner or device may be provided to include the above programming. Representative optical scanners of interest include those described in U.S. Pat. Nos. 5,585,639; 5,760,951; 5,763,870; 6,084, 991; 6,222,664; 6,284,465; 6,329,196; 6,371,370 and 6,406,849—the disclosures of which are herein incorporated by reference. An exemplary optical scanner as may be used in the present invention is shown in FIG. 1.

Referring now to FIG. 1, an apparatus of the present invention (which may be generally referenced as an array "scanner") is illustrated. A light system provides light from a laser 100 that passes through an electro-optic modulator (EOM) 110 with attached polarizer 120. Each laser 100*a*, 100*b* may be of different wavelength (e.g., one providing red light and the other green) and each has its own corresponding EOM 110*a*, 110*b* and polarizer 120*a*, 120*b*. The beams may be combined along a path toward a holder or caddy 200 by the use of full mirror 151 and dichroic mirror 153. A control signal in the form of a variable voltage applied to each corresponding EOM 110*a*, 110*b* by the controller (CU) 180, changes the polarization of the exiting light which is thus more or less attenuated by the corresponding polarizer 120*a*, 120*b*. Controller 180 may be or include a suitably programmed processor. Thus, each EOM 110 and corresponding polarizer 120 together act as a variable optical attenuator which can alter the power of an interrogating light spot exiting from the attenuator. The remainder of the light from both lasers 100*a*, 100*b* is transmitted through a dichroic beam splitter 154, reflected off fully reflecting mirror 156 and focused onto an array mounted on holder 200, using optical components in beam focuser 160. Light emitted (in particular, fluorescence) at two different wavelengths (e.g., green and red light) from features on the array, in response to the interrogating light, is imaged using the same optics in focuser/scanner 160, and is reflected off mirrors 156 and 154. The distinct excitation sources are aligned such that the emitted fluorescence passes through a further dichroic mirror 158 and are passed to respective detectors 150*a* and 150*b* More optical components (not shown) may be used between the dichroic mirror and each detector 150*a*, 150*b* (such as lenses, pinholes, filters, fibers, etc.), where each detector 150*a*, 150*b* may be of various different types (e.g., a photo-multiplier tube (PMT) or a CCD or an avalanche photodiode (APD)). All of the optical components through which light emitted from an array 12 or calibration member 230 in response to the illuminating laser light, passes to detectors 150*a*, 150*b*, together with those detectors, form a detection system. This detection system has a fixed focal plane. A scan system causes the illuminating region in the form of a light spot from each laser 100*a*, 100*b*, and a detecting region of each detector 150*a*, 150*b* (which detecting region will form a pixel in the detected image), to be scanned across multiple regions of an array or array package mounted on holder 200. The scanned regions for an array will include at least the multiple features of the array. In particular the scanning system is typically a line by line scanner, scanning the interrogating light in a line across an array when at the reading position, in a direction of arrow 166, then moving ("transitioning") the interrogating light in a direction into/out of the paper as viewed in FIG. 1 to a position at an end of a next line, and repeating the line scanning and transitioning until the entire array has been scanned. This scanning feature is accomplished by providing a housing 164 containing mirror 158 and focuser 160, which housing 164 can be moved along a line of pixels by a transporter 162. The second direction 192 of scanning (line transitioning) can be provided by second transporter that may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The reader of FIG. 1 may further include a reader (not shown) that reads an identifier from an array package. When identifier 40 is in the form of a bar code, that reader may be a suitable bar code reader.

Of course, the movements 166 and 192 may be accomplished by actuating holder 200 or housing 164 alone. Still further, the movement roles described for each element above may be swapped.

A device for measuring signal focus error, e.g., a position sensitive detector 170, is provided to sense any offset between a region of an array when in the reading position, and a determined position of the focal plane of the detection system. The autofocus system includes detector 170, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, a position detector 202 e.g. a quadrature position encoder, also feeding back to the CU measures the absolute position (i.e., relative to the apparatus) of the servo-controlled adjuster 190). As above with respect to movements 166 and 192, it should be observed that focus servo control movement 196 may occur in connection with housing 164 instead of the holder, or, if the detection system is not a fixed focal plane system, by an adjustment of laser focuser 160. Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors.

Controller 180 of the apparatus is connected to receive signals from detectors 150*a*, 150*b* (these different signals being different "channels"), namely a signal which results at each of the multiple detected wavelengths from emitted light for each scanned region of array 12 when at the reading position mounted in holder 200. Controller 180 may analyze, store, and/or output data relating to emitted signals received from detectors 150*a*, 150*b* in a known manner.

Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40).

As indicated above, scanner devices according to the subject invention are devices that are capable of automatically selecting a dye specific scale factor in response to input dye selections, as described above. The subject scanners can readily be produced by recording the relevant programming/information, as described above, into controlling firmware/software of the device, e.g., by copying files into a storage medium of the device, by loading the device with a computer readable medium that includes the subject programming/information, and the like.

In certain embodiments, a master set of nominal scale factors (optionally including crosstalk characteristics) for a plurality of dyes may be obtained using one scanner and then employed with a plurality of additional scanners, so that the nominal scale factor information obtained in a first scanner is used in multiple additional scanners. Alternatively, the nominal scale factor/crosstalk information can be generated de novo for each scanner, such that a given scanner employs information that was generated with it, and not some other scanner.

Utility

The subject biopolymer optical scanners find use in a variety of different applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of including the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest that may be practiced using the subject arrays include: gene discovery assays, differential gene expression analysis assays; nucleic acid sequencing assays, and the like. References describing methods of using arrays in various applications include U.S. Pat. Nos. 5,143, 854; 5,288,644; 5,324,633; 5,432,049; 5,470,710; 5,492, 806; 5,503,980; 5,510,270; 5,525,464; 5,547,839; 5,580, 732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436, 170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a programmed scanner according to the present invention, the array will typically be exposed to a sample (such as a fluorescently labeled analyte, e.g., protein containing sample) and the array then read.

In one mode of operation, an array in a package is typically first exposed to a liquid sample. This liquid sample may be placed directly on the array or introduced into a chamber through septa in the housing of the array. After a time to allow binding of respective binding pair members, for example via hybridization, the array may then be washed and scanned with a liquid (such as a buffer solution) present in the chamber and in contact with the array, or it may be dried following washing. After mounting a given array in cradle 200 (either with the array features on the glass surface nearer to, or further from, the lens—depending, at least, upon the lens setup) the identifier reader may automatically (or upon operator command) read an identifier from the array package, which may be used to e.g. retrieve information on the array layout from a database containing the identifier in association with such information. Such a database may be a local database accessible by controller 180 (such as may be contained in a portable storage medium in drive 182.

Following contact of the array with the sample being assayed, as described above, the array is then read by an array scanner according to the subject invention. At some point prior to reading the array, the one or more specific dyes employed in the assay are input into the scanner, e.g., via user input of the information into a graphic user interface (GUI) of the scanner. For example, where a given array is one that has been contacted with a sample or samples in which the targets are labeled with Cy3 and Cy5, the user inputs the specific dye information, i.e., Cy3 and Cy5 into the scanner, e.g., via the GUI of the scanner. The identity of the dyes employed could also be encoded in the array barcode, read by the scanner and implemented automatically. For example, the barcode on the array may include information regarding the particular dyes that are used with the array, such that the scanner reads the barcode, obtains dye input and selects the appropriate scale factor to employ. The dye input information on the barcode may be based on particular dyes with which the array is provided, e.g., in a purchased kit, etc., or based on particular dyes for which the array is specifically designed for use. Following input of the specific dye information, the scanner then automatically selects a dye specific scale factor for each input dye, as described above, to employ in reading the array. Reading of the array may be accomplished by illuminating the array and reading the location and intensity of resulting fluorescence at each feature of the array to detect any binding complexes on the surface of the array.

It is further noted that aspects of the invention may be applicable to a variety of optical scanners including those that detect chemiluminescent or electroluminescent labels.

In any case, results from reading an array may be raw results (such as fluorescence intensity readings for each feature in one or more color channels) or may be processed results such as obtained by deconvoluting a reading to remove/subtract crosstalk, rejecting a reading for a feature which is below a predetermined threshold and/or forming conclusions based on the pattern read from the array (such as whether or not a particular target sequence may have been present in the sample).

The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc.

Kits

Kits for use in connection with the subject invention may also be provided. Such kits preferably include at least a computer readable medium including programming as discussed above and instructions. The instructions may include installation or setup directions. The instructions may include directions for use of the invention with options or combinations of options as described above. In certain embodiments, the instructions include both types of information. Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

It is evident from the above results and discussion that the subject invention provides for greatly improved bipolymeric array scanning devices. The devices of the subject invention are sufficiently flexible so that they can be employed with a number of different dyes and still employ an actual scale factor for each dye that can be equated to a known master scale factor. By automatically selecting the dye specific scale factor for a given dye, the subject scanning devices save the user from having to manually adjust the instrument gain to obtain a dye specific scale factor and/or process the data to account for the use of an incorrect scale factor. Accordingly, the subject invention provides a number of benefits. One benefit provided by the subject invention is the ability to hold the apparent scale factor equal to one or more master scale factors regardless of the specific dye that is employed. This feature provides the user with consistent data from several dyes without the need for post-processing of these data. The subject invention also provides the opportunity for deconvolution and subtraction of first-order crosstalk, and minimization of saturation due to such crosstalk. Further, it allows for the ability to determine when crosstalk noise is interfering with feature detection or pixel saturation and alter the system parameters accordingly to minimize this affect. Accordingly, the subject invention provides users with more consistent data, more dye flexibility and less frequent saturation with less manual effort on their own part, and fewer features with signal to noise decreased, or pixels saturated, by crosstalk noise. As such, the present invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of obtaining a collection of nominal scale factors, said method comprising:
    measuring the number of counts per dye density for each of at least three different optically detectable labels using an optical multi-channel detector scanner having a gain set at a nominal value; and
    determining a nominal scale factor for each of said at least three different optically detectable labels from said measuring to obtain said collection of nominal scale factors, wherein said nominal scale factors are measured counts per dye density.

2. The method according to claim 1, wherein said optically detectable labels are fluorescent dyes.

3. The method according to claim 2, wherein each nominal scale factor of said collection is determined by measuring the number of counts per dye density for each dye member of said plurality, wherein said measuring is made for each member at the same nominal scanner gain setting of said optical scanner.

4. The method according to claim 2, wherein said collection comprises nominal scale factors for at least 5 different dyes.

5. The method according to claim 2, wherein said collection comprises nominal scale factors for at least 10 different dyes.

6. The method according to claim 2, wherein said method further comprises determining first order crosstalk for each of said plurality of dyes and said method is a method of obtaining a collection of nominal scale factors and first order crosstalk for each of said plurality.

7. The method according to claim 6, wherein said first order crosstalk for each member dye of said plurality is determined by measuring off-diagonal terms linking said member dye in a first measurement channel of said scanner into signal observed in at least a second measurement channel of said scanner.

8. The method according to claim 2, wherein said method further comprises recording said collection onto a computer readable medium.

9. A method of programming a first scanner, said method of programming scanner comprising:
    inputting a collection of nominal scale factors obtained according to the method of claim 1 into said scanner.

10. The method of programming a scanner according to claim 9, wherein said inputting comprises employing said scanner to measure said nominal scale factors that make up said collection.

11. The method of programming a scanner according to claim 9, wherein said inputting comprises employing a second scanner to obtain said collection and then inputting said collection into said first scanner.

12. The method of programming a scanner according to claim 9, wherein said collection further comprises first order crosstalk data for each member of said plurality.

* * * * *